(12) United States Patent
Chava et al.

(10) Patent No.: US 7,678,903 B2
(45) Date of Patent: Mar. 16, 2010

(54) PROCESS FOR THE PREPARATION OF LEVOFLOXACIN HEMIHYDRATE

(75) Inventors: Satya-naryana Chava, Secunderabad (IN); Seeta Ramanjaneyulu Gorantla, Secunderabad (IN); Venkata Panakala Rao, Hyderabad (IN)

(73) Assignee: Matrix Laboratories Limited, Bollaram (IN)

( * ) Notice: Subject to any disclaimer, the term of this patent is extended or adjusted under 35 U.S.C. 154(b) by 373 days.

(21) Appl. No.: 11/662,945

(22) PCT Filed: Aug. 8, 2005

(86) PCT No.: PCT/IN2005/000264

§ 371 (c)(1),
(2), (4) Date: Apr. 3, 2007

(87) PCT Pub. No.: WO2006/030452

PCT Pub. Date: Mar. 23, 2006

(65) Prior Publication Data

US 2008/0097095 A1     Apr. 24, 2008

(30) Foreign Application Priority Data

Sep. 17, 2004    (IN) .......................... 931/CHE/2004

(51) Int. Cl.
*C07D 498/06*    (2006.01)
(52) U.S. Cl. .................................... 544/101; 514/230.2
(58) Field of Classification Search .................. 544/101
See application file for complete search history.

(56) References Cited

FOREIGN PATENT DOCUMENTS

| EP | 444678 A1 | * | 9/1991 |
| WO | WO 03028664 A2 | * | 4/2003 |

\* cited by examiner

*Primary Examiner*—Kahsay T Habte
(74) *Attorney, Agent, or Firm*—Blank Rome LLP

(57) ABSTRACT

The present invention relates to an improved process for the preparation of Levofloxacin hemihydrate by adjusting the moisture content of the solvent to about 12% to about 20% during crystallization.

13 Claims, No Drawings

PROCESS FOR THE PREPARATION OF LEVOFLOXACIN HEMIHYDRATE

The present invention relates to a process for the preparation of Levofloxacin hemihydrate.

BACKGROUND OF THE INVENTION

Levofloxacin, (S)-9-fluoro-2,3-dihydro-3-methyl-10-(4-methyl-1-piperazinyl)-7-oxo-7H-pyrido[1,2,3-de]-1,4-benzoxazine-6-carboxylic acid has the formula as given below

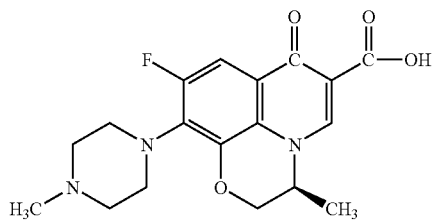

Levofloxacin

Levofloxacin is the S-enantiomer of Ofloxacin, a fluoroquinolone antibacterial agent. The mechanism of action of Levofloxacin and other fluoroquinolone antibacterials involves the inhibition of DNA gyrase (bacterial topolsomerase II), an enzyme required for DNA replication, transcription repair and recombination.

U.S. Pat. No. 4,383,892 discloses the pyrido [1,2,3-de][1,4] benzoxazine derivatives and methods for preparation of them.

U.S. Pat. No. 5,053,407 discloses the optically active pyridobenzoxazine derivatives, intermediates useful for preparation of pyridobenzoxazine derivatives and the process.

U.S. Pat. No. 5,051,505 discloses the process for preparation of piperazinyl quinolone derivatives by reaction of dihaloquinolones with piperazine derivatives and tetra alkyl ammonium halides in presence of a polar solvent such as acetonitrile, DMF, pyridine, sulfolane and DMSO. U.S. Pat. No. 5,155,223 discloses the process for preparation of quinoline carboxylic acids.

Three polymorphic forms of levofloxacin i.e. anhydrous levofloxacin form α, β, γ and two hydrate forms i.e. hemihydrate and monohydrate are reported in the literature.

U.S. Patent Application No. 2003/130507 discloses the process for preparation of levofloxacin by reaction of (S)-(-) 9,10-difluoro-3-methyl-7-oxo-2,3-dihydro-7H-pyrido[1,2,3-de][1,4] benzoxazine-6-carboxylic acid with N-methyl piperazine in a polar solvent or as a neat mixture at an elevated temperature of 70° C. to 120° C. and recovering levofloxacin by using the techniques well known in the art. The Application further discloses the polymorphic or pseudomorphic forms (form-A, form-B, form-C, form-F, form-G, form-H) of levofloxacin and the processes for their preparation.

EP Patent No. 444,678 and U.S. Pat. No. 5,545,737 are particularly disclosed the processes for preparation of hemihydrate free of monohydrate by crystallizing crude levofloxacin in aqueous ethanol containing 2-10% moisture content and process for monohydrate free of hemihydrate by crystallizing crude levofloxacin in aqueous ethanol containing 10% or more than 10% moisture content.

Surprisingly, the inventors observed that when the water content is varied or by addition of water to the slurry of levofloxacin in a polar solvent at the reflux temperature of the solvent, levofloxacin hemihydrate free of the monohydrate resulted.

SUMMARY OF THE INVENTION

The main object of the present invention is to provide an alternate process for the preparation of levofloxacin hemihydrate free of levofloxacin monohydrate.

The process for the preparation of levofloxacin hemihydrate is shown in the following scheme.

Accordingly in the present invention reacting (S)-(-) 9,10-difluoro-3-methyl-7-oxo-2,3-dihydro-7H-pyrido[1,2,3-de][1,4] benzoxazine-6-carboxylic acid with N-methyl piperazine yields crude levofloxacin. Suspending crude levofloxacin in isopropanol, addition of known quantity of water to make-up the water content to about 12% to about 20% followed by precipitation affords the levofloxacin hemihydrate.

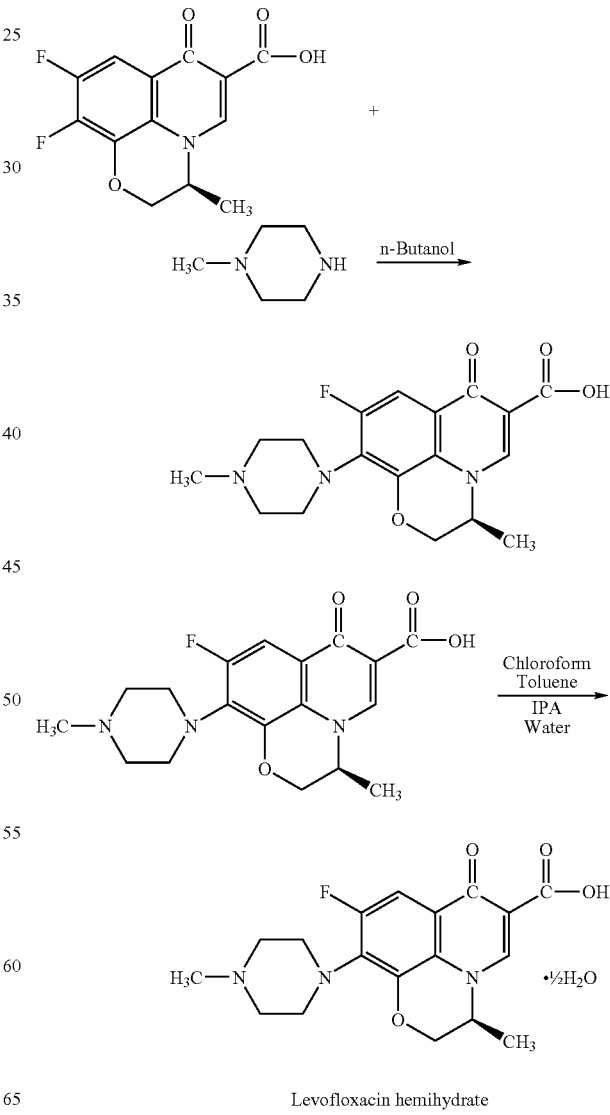

Levofloxacin hemihydrate

The prepared levofloxacin hemihydrate is identical with the reported levofloxacin hemihydrate by its X-ray diffraction pattern.

DETAILED DESCRIPTION OF THE INVENTION

Thus in accordance with the present invention levofloxacin hemihydrate is prepared by reacting (S)-(-)9,10-difluoro-3-methyl-7-oxo-2,3-dihydro-7H-pyrido [1,2,3-de][1,4] benzoxazine-6-carboxylic acid with N-methyl piperazine in a polar solvent preferably n-Butanol at temperature of 120° C. to 125° C. for about 5 hrs to 12 hrs followed by removing the solvent by vacuum distillation at temperature below 100° C. Toluene is added to the reaction mass followed by chloroform and mixed for about 30 min at temperature of 20° C. to 40° C. Removed the insolubles by filtration and the solvent mixture is removed by distillation at temperature below 60° C. Isopropanol is added to the reaction mass, cooled, mixed for about 30 min to about 4 hrs at temperature of 20° C. to 40° C. and isolated the levofloxacin crude.

Levofloxacin crude is dissolved in mixture of toluene-chloroform at temperature of 20° C. to 40° C. by mixing for about 30 min to 2 hrs. Removed the insolubles by filtration, treated the clear solution with carbon and distilled off the toluene-chloroform at temperature below 60° C. Isopropanol is added to the mass, temperature is raised to 65° C. to 90° C., known quantity of water preferably to make-up the water content about 12% to about 20%, more selectively about 15% is added to the reaction mass at temperature of 60° C. to 90° C., mixed for about 5 min to 30 min, cooled to 15° C. to about 35° C., mixed for about 30 min to 4 hrs, isolated and dried at temperature of 45° C. to 85° C. preferably at 60° C. to 70° C. gives the levofloxacin hemihydrate.

The required (S)-(-) 9,10-difluoro-3-methyl-7-oxo-2,3-dihydro-7H-pyrido [1,2,3-de][1,4] benzoxazine-6-carboxylic acid is prepared by the reported method.

The present invention is further illustrated with the following example.

EXAMPLE

Preparation of Levofloxacin Hemihydrate

Step-1

(S)-(-) 9,10-difluoro-3-methyl-7-oxo-2,3-dihydro-7H-pyrido[1,2,3-de][1,4]benzoxazine-6-carboxylic acid (100 g) is suspended in n-Butanol (80 ml), N-methyl piperazine (80 g) is added and the temperature is raised to 120° C.-125° C. Reaction mass is maintained at temperature of 120° C.-125° C. for 6 hrs and cooled to below 100° C., distilled off the solvent under vacuum at temperature below 100° C. Toluene (100 ml) is added and again distilled off under vacuum to remove traces of n-Butanol. Reaction mass is cooled to 60° C.-65° C., toluene (200 ml) and chloroform (1000 ml) are added and mixed for about 60 min at 25° C.-30° C. The reaction mass is filtered to remove insolubles. Clear filtrate is collected and the solvents are distilled off under vacuum at temperature below 65° C. Isopropanol (500 ml) is added to the reaction mass, temperature is raised to reflux and maintained at reflux temperature for about 15 min at 75° C.-80° C. Reaction mass is cooled to 25° C.-30° C., maintained for 1 hr at 25° C.-30° C., the product is filtered and washed the wet cake with isopropanol (50 ml).

The weight of the wet cake is about 150 g and the wet cake as such is preceded to next step without drying.

Step-2

The above-obtained wet cake (150 g) is dissolved in a mixture of toluene (500 ml) and chloroform (2000 ml). Activated carbon (10 g) is added and stirred for about 30 min at 25° C.-30° C. The reaction mass is filtered, filtrate is collected and distilled off the solvents under vacuum at temperature below 60° C. Isopropanol (50 ml) is added to the mass and distilled off under vacuum at temperature below 60° C. Isopropanol (425 ml) is added to the mass and temperature of reaction mass is raised to reflux. Water (75 ml) is added slowly over 15 min and maintained for about 15 min at reflux temperature. Reaction mass is cooled to 30° C. and maintained for about 30 min at 25° C.-30° C. Product is filtered and dried at 60° C.-70° C. till constant weight.

The dry weight of Levofloxacin hemihydrate is 90 g (68.5%)

The water content is 2.54% (by KF)

The IR and XRD of the product are identical with the reported data of Levofloxacin hemihydrate.

We claim:

1. A process for the preparation of Levofloxacin hemihydrate comprising the steps of:
    reacting (S)-(-)9,10-difluoro-3-methyl-7-oxo-2,3-dihydro-7H-pyrido[1,2,3-de][1,4] benzoxazine-6-carboxylic acid with N-methyl piperazine in n-butanol at a temperature of 120° C. to 125° C.;
    removing the n-butanol under vacuum at a temperature below 100° C.;
    dissolving the residue in a mixture of toluene-chloroform and removing insolubles therefrom;
    removing the toluene-chloroform mixture and adding isopropanol;
    adding a pre-determined quantity of water and mixing for about 5 min to about 30 min;
    cooling to a temperature of about 15° C. to about 35° C.; and
    isolating and drying the product.

2. The process as claimed in claim 1, wherein the mixture of toluene-chloroform is removed under vacuum below 60° C.

3. The process as claimed in claim 1, wherein the crude Levofloxacin is isolated at 20° C. to 30° C.

4. The process as claimed in claim 1, wherein the water is added at a temperature of between 60° C. to 90° C.

5. The process as claimed in claim 1, wherein the pre-determined quantity of water added is equivalent to between 12% to 20% of the isopropanol.

6. The process as claimed in claim 1, wherein the drying is carried out at a temperature of 45° C. to 85° C.

7. A process for the preparation of Levofloxacin hemihydrate free of Levofloxacin monohydrate, comprising the steps of:
    providing an amount of (S)-(−)9,10-difluoro-3-methyl-7-oxo-2,3-dihydro-7-H-pyrido[1,2,3-de][1,4] benzoxazine-6-carboxylic acid;
    suspending the same in n-butanol to form a first solution;
    adding a molar excess amount of N-methyl piperazine to the first solution;
    heating the first solution to a temperature substantially the same as the reflux temperature of the n-butanol;
    removing the n-butanol at a temperature below 100° C. to form a residue;
    washing the residue with a quantity of isopropanol to form a second solution;
    heating the second solution to a temperature substantially the same as the reflux temperature of the second solution;

adding a pre-determined quantity of water to the second solution for a sufficient amount of time to form the Levofloxacin hemihydrate, wherein the amount of water added is equivalent to between about 12% to 20% of the quantity of isopropanol; and isolating the Levofloxacin hemihydrate.

8. The process as claimed in claim 7, further comprising the steps of:

dissolving the residue in a mixture of toluene-chloroform;

removing insolubles therefrom; and removing the toluene-chloroform under vacuum below a temperature of about 60° C.

9. The process as claimed in claim 7, wherein the amount of water added is added to the second solution at a temperature of between about 60° to 90° C.

10. The process as claimed in claim 7, further comprising the step of drying the Levofloxacin hemihydrate at a temperature of between about 45° C. to 85° C.

11. The process as claimed in claim 7, further comprising the step of drying the Levofloxacin hemihydrate at a temperature of between about 60° C. to 70° C.

12. The process as claimed in claim 7, wherein the amount of water added is equivalent to 15% of the quantity of isopropanol.

13. The process as claimed in claim 7, wherein the sufficient amount of time to form the Levofloxacin hemihydrate is between about 30 min and 4 hrs.

* * * * *